United States Patent
Achard et al.

(10) Patent No.: US 10,563,285 B2
(45) Date of Patent: *Feb. 18, 2020

(54) METHOD FOR INSPECTING A LIQUID METAL BY ULTRASOUNDS

(71) Applicant: CONSTELLIUM ISSOIRE, Issoire (FR)

(72) Inventors: Jean-Louis Achard, Vizille (FR); Pierre Le Brun, Saint Jean de Soudain (FR)

(73) Assignee: CONSTELLIUM ISSOIRE, Issoire (FR)

( * ) Notice: Subject to any disclaimer, the term of this patent is extended or adjusted under 35 U.S.C. 154(b) by 139 days.

This patent is subject to a terminal disclaimer.

(21) Appl. No.: 15/516,623

(22) PCT Filed: Oct. 6, 2015

(86) PCT No.: PCT/FR2015/052680
§ 371 (c)(1),
(2) Date: Apr. 3, 2017

(87) PCT Pub. No.: WO2016/055729
PCT Pub. Date: Apr. 14, 2016

(65) Prior Publication Data
US 2017/0306441 A1    Oct. 26, 2017

(30) Foreign Application Priority Data
Oct. 7, 2014    (FR) ..................... 14 02257

(51) Int. Cl.
*G01N 33/205*    (2019.01)
*C22B 9/02*    (2006.01)
(Continued)

(52) U.S. Cl.
CPC .............. *C22B 9/026* (2013.01); *B06B 3/00* (2013.01); *C22B 21/06* (2013.01); *G01N 29/032* (2013.01);
(Continued)

(58) Field of Classification Search
CPC .................................................. G01N 33/205
See application file for complete search history.

(56) References Cited

U.S. PATENT DOCUMENTS 3,131,514 A * 5/1964 Metta ................. E04C 2/20
                                                  156/242
3,444,726 A * 5/1969 Pitcher ............ G01N 29/032
                                                   73/61.75
(Continued)

FOREIGN PATENT DOCUMENTS

EP    1724559 A2    11/2006

OTHER PUBLICATIONS

International Search Report of PCT/FR2015//052680 dated Feb. 11, 2016.
(Continued)

*Primary Examiner* — Peter J Macchiarolo
*Assistant Examiner* — Alexander A Mercado
(74) *Attorney, Agent, or Firm* — McBee Moore Woodward & Vanik IP, LLC

(57) ABSTRACT

The method comprises the following steps:
  a) Providing a sonotrode (1) formed from an essentially inert material with respect to the liquid metal, such as a ceramic, and preferably a silicon nitride or a silicon oxynitride, such as SIALON, or a metal essentially inert to said liquid metal,
  b) Immersing at least partially the sonotrode (1) in a bath of said metal, (Continued)

c) Applying to the sonotrode (1) power ultrasounds, particularly ultrasounds having a power greater than 10 watts to obtain the wetting of said sonotrode by said metal,
d) Applying continuously to the sonotrode (1) measurement ultrasounds, also known as testing ultrasounds, particularly ultrasounds wherein the frequency is between 1 and 25 MHz,
e) Applying intermittently to the sonotrode (1) power ultrasounds, particularly ultrasounds having a power greater than 10 watts, to maintain said wetting.

20 Claims, 2 Drawing Sheets

(51) Int. Cl.
    *B06B 3/00*     (2006.01)
    *C22B 21/06*     (2006.01)
    *G01N 29/032*     (2006.01)
    *G01N 29/22*     (2006.01)

(52) U.S. Cl.
    CPC ......... *G01N 29/228* (2013.01); *G01N 33/205* (2019.01); *Y02P 10/234* (2015.11)

(56) References Cited

U.S. PATENT DOCUMENTS

| | | | | |
|---|---|---|---|---|
| 4,116,766 A | * | 9/1978 | Poindexter | G21C 13/0735 376/203 |
| 4,261,197 A | * | 4/1981 | Mansfield | B06B 3/00 73/61.79 |
| 4,287,755 A | * | 9/1981 | Mansfield | G01N 29/228 73/61.79 |
| 4,563,895 A | * | 1/1986 | Eckert | G01N 29/228 73/61.75 |
| 4,662,215 A | * | 5/1987 | Eckert | G01N 29/228 73/61.75 |
| 5,604,301 A | * | 2/1997 | Mountford | B01D 21/283 73/54.31 |
| 5,708,209 A | * | 1/1998 | Stiffler | A61B 8/546 73/644 |
| 6,886,406 B1 | * | 5/2005 | Couet | B08B 3/12 73/1.49 |
| 2004/0200269 A1 | * | 10/2004 | Muller | G01N 29/032 73/61.75 |
| 2006/0150718 A1 | * | 7/2006 | Ducret | G01N 29/11 73/73 |
| 2010/0218608 A1 | * | 9/2010 | Eckert | G01F 1/662 73/584 |
| 2010/0218617 A1 | * | 9/2010 | Eckert | G01F 1/662 73/861.27 |
| 2012/0042751 A1 | * | 2/2012 | Rundquist | C22B 21/064 75/646 |

OTHER PUBLICATIONS

Ono et al. "An On-Line Ultrasonic Cleanliness Analyzer for Molten Light Metals" JOM. (Feb. 2004) pp. 59-64.

Ono et al., "Ultrasonic Techniques for Imaging and Measurements in Molten Aluminum" IEEE Trnasactions on Ultrasoncics Ferroelectrics and Freqauency Contrl. (Dec. 2003) vol. 50, Mp. 12: 1711-1721.

* cited by examiner

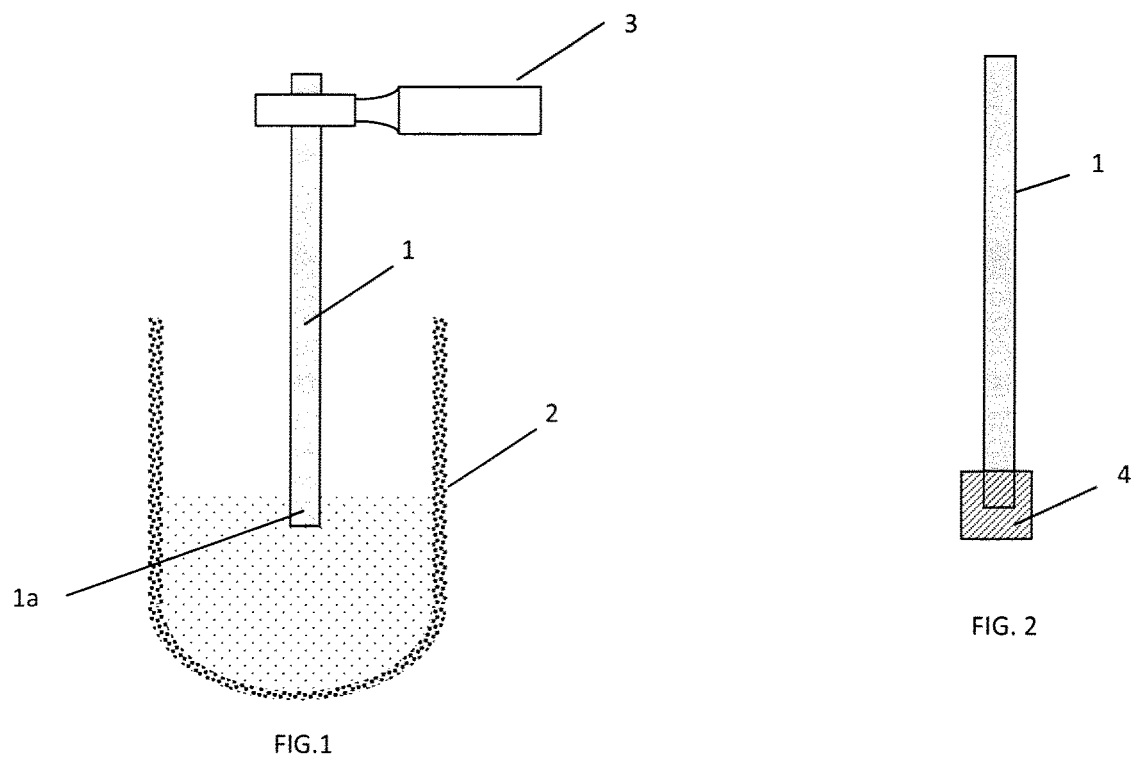
FIG.1
FIG. 2
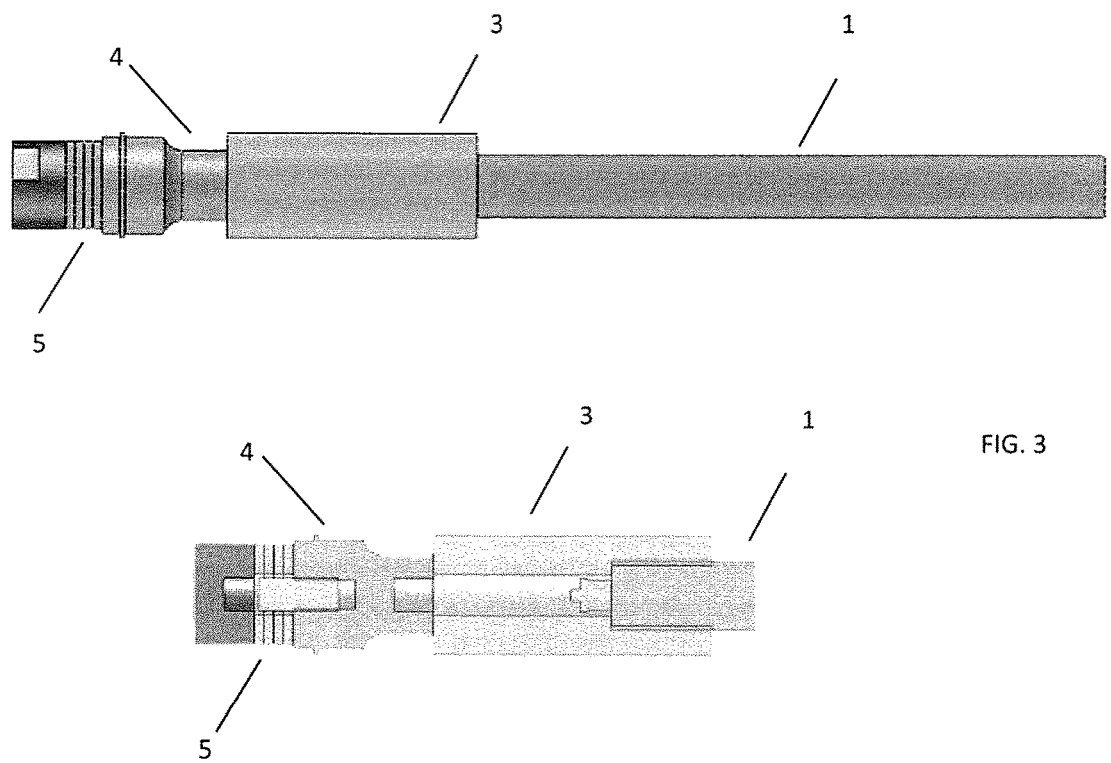
FIG. 3

METHOD FOR INSPECTING A LIQUID METAL BY ULTRASOUNDS

CROSS REFERENCE TO RELATED APPLICATIONS

This application is a § 371 National State Application of PCT/FR2015/052680, filed Oct. 6, 2015, which claims priority to French Application No. 1402257 filed Oct. 7, 2014.

BACKGROUND OF THE INVENTION

The invention relates to the field of sonic non-destructive testing and analysis of liquid metal. More specifically, the invention relates to an enhanced method using at least a sonotrode made of ceramic or refractory metal, i.e. inert with respect to the liquid metal enabling optimised ultrasound transmission for the purposes of testing, and analysis.

DESCRIPTION OF RELATED ART

In the field of liquid metal casting, it is of the utmost importance to accurately control the inclusion quality. Indeed, thereupon depends the quality and rejection rate of sheet metal or parts particularly sheets or thin parts, in particular those obtained during the manufacture of closed receptacles such as beverage or aerosol cans. In the case of liquid metals, this measurement is particularly delicate due to the low number of inclusions present in the liquid metal, but the harmfulness whereof is high. Generally, the inclusion quality is determined by the rate of inclusions contained in a liquid metal and by the size thereof.

It is essentially based on liquid metal sampling methods, wherein the inclusions are concentrated on a filter before being observed and counted by metallography. Such is the case of the so-called PoDFA (acronym for Porous Disk Filtration of Aluminium) method in the case of liquid aluminium, but this method is merely indicative of size and number of inclusions.

A method referred to as LiMCA (acronym for Liquid Metal Cleanliness Analysis) is also known in this field, essentially consisting of sampling the liquid metal continuously via a small orifice and measuring therein the variation in resistance of the liquid metal at each inclusion passage. However, this apparatus, operating according to the Coulter meter principle, has the drawbacks of restriction in terms of analysed quantity (approximately 0.01% of the cast metal) and detectable size (between 15 and 150 µm approximately).

More recently, an apparatus was developed which uses the filtration rate to give a qualification of the level of inclusion cleanliness. Such is the case in particular of the Prefil® method. In these methods, the sampling frequencies feasible in practice are low, and the volume fraction analysed remains as such low (practical order of magnitude of 0.01% of cast metal).

The need to develop a continuous measurement method, particularly when the metal circulates in a trough, dates back to the 1960s.

As such, Reynolds explored the approach of sonic measurement for evaluating the inclusion quality of liquid aluminium, which is expected to allow access to a much larger fraction of the liquid metal (several percent at least).

The equipment developed at the time, known as "Reynolds 4M", had a limited sensitivity and appears to have only been used qualitatively via a quality index capable of differentiating clean metal from very soiled metal.

It was the subject matter of the patent application U.S. Pat. No. 4,287,755 by "Reynolds Metals Company" in 1979, and the publication by Mansfield, T. L., "Molten Aluminum Quality Measured with Reynolds 4M System".

In more recent developments in respect of ultrasounds, note should be taken of the "MV20/20" apparatus from "Metalvision", available on the market and described in the publication "An ultrasonic sensor for the continuous online monitoring of the cleanliness of liquid aluminium", TMS2005. It gives, in real-time, an indication of the size and number of inclusions present in the liquid metal, but without any associated calibration method. This apparatus is only used very infrequently, and in any case not on a large scale, essentially due to the lack of reliability thereof. It is particularly noted that the waveguide, or sonotrode, is made of steel, reacts with metal, which gives rise to a change of the interface and thus of the wave transmission quality and level.

At the end of the 1990s, the applicant, "Pechiney Rhenalu", also developed sonic measurement of inclusions and filed in particular, in 1999, the application FR2 796 155 relating to a method for calibrating the size of defects viewed by ultrasound in liquid metal, entitled "Improved method and device for counting inclusions in a liquid metal bath with ultrasounds". However, these various works, while providing a calibration method, did not make it possible to ensure the reliability of the method for sonic detection/counting of the inclusions present in liquid metal while nonetheless demonstrating that it made it possible to analyse a larger fraction of the liquid metal. This restricted reliability is due in particular to the lack of stability of the waveguide/liquid metal interface. It is indeed known that the waveguides need to be wetted by the liquid metal to enable the transmission of the energy to the liquid metal without excessive losses. For this reason, the waveguides used are made of metal, particularly steel or titanium.

However, this is not sufficient to obtain perfect wetting, and methods have been developed to improve same. Evidence of this, in the context of liquid aluminium, is particularly found in the patent EP0035545B1, subject to a priority date of 1979, held by "Reynolds Metal Company" claiming the vapour phase deposition of an aluminium film on a titanium sonotrode. However, in fact, even in such a design, the wetting quality varies during use due to the reaction of the waveguide material with the liquid metal and the sonotrode with the deposition thereof is not reusable.

Refractory metals are not used in liquid metals specifically because they are not wetted by said liquid metals. Only a chemical deposition method would make it possible to obtain wetting, but for a limited time, which is not reliable, practical or economical.

Therefore, there is not currently a method capable of reliably detecting inclusions in a large fraction of cast metal.

SUMMARY

One of the aims of the present invention thus consists of remedying at least one of the abovementioned drawbacks. To this end, the present invention relates to a method for sonic testing of a liquid metal comprising the following steps:

a) Providing a sonotrode (1) formed from a substantially inert material with respect to the liquid metal, such as a ceramic, and preferably a silicon nitride or a silicon oxynitride, such as SIALON, or a metal substantially inert to said liquid metal, b) Immersing at least partially the sonotrode (1) in a bath of said metal, c) Applying to the sonotrode (1) power ultrasounds, particularly ultrasounds having a power greater than 10 watts to obtain the wetting of said sonotrode by said metal, d) Applying continuously to the sonotrode (1) measurement ultrasounds, also known as testing ultrasounds, particularly ultrasounds wherein the frequency is between 1 and 25 MHz, e) Applying intermittently to the sonotrode (1) power ultrasounds, particularly ultrasounds having a power greater than 10 watts, to maintain said wetting and ensure the stability of the signal over time.

BRIEF DESCRIPTION OF THE DRAWINGS

FIGS. 1-7 depict embodiments as described herein.

DETAILED DESCRIPTION OF A PREFERRED EMBODIMENT

Figure 4:
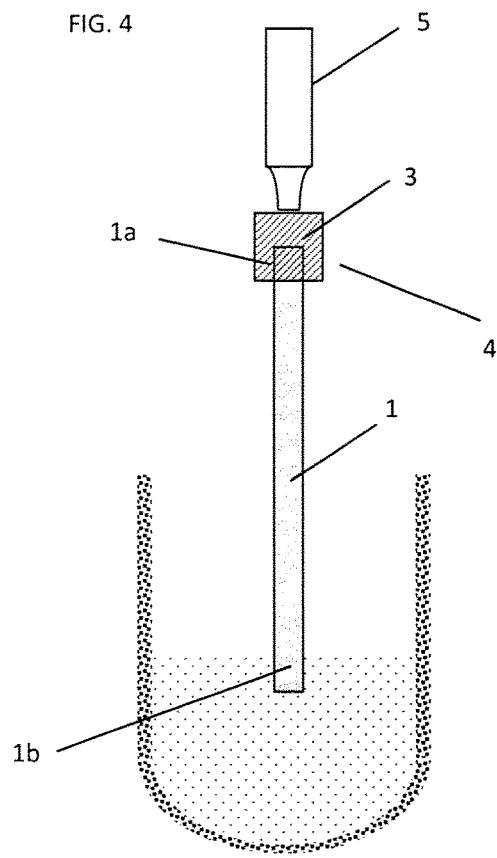

As such, the wetting of the sonotrode by the liquid metal is maintained durably, particularly over several days, by merely applying power ultrasounds to the sonotrode immersed in the liquid metal. In step b), the sonotrode is immersed in a liquid metal bath.

Power ultrasounds are applied to the sonotrode in step c) and make it possible to obtain wetting by the liquid metal. By means of this method, it is then possible to obtain optimised ultrasound transmission to the liquid metal which is durable and stable over time.

Advantageously, the application of power ultrasounds in step e) is carried out intermittently. Indeed, the wetting of the sonotrode resists over time such that the application of power ultrasounds for maintaining wetting can be sporadic.

In respect of step d), it further comprises the application of measurement ultrasounds to the sonotrode, particularly ultrasounds wherein the frequency is between 1 and 25 MHz. It is then possible to use the sonotrode wetted previously in step c) for applications such as non-destructive testing of the liquid metal by applying measurement ultrasounds to the sonotrode over a long period.

As such, the ultrasound measurement is performed continuously so as to be able to analysis in-line the inclusion quality of the liquid metal and particularly in a trough, before the treatment thereof or before casting in a casting mould. Indeed, the invention enables the concomitant application of measurement ultrasounds for treatment and of intermittent power ultrasounds for regeneration of wetting, which tends to degrade over time, simply due to the effect of long-term maintenance or by the presence in contact with the sonotrode of gases, oxides or other impurities.

According to one advantageous embodiment, the liquid metal is liquid aluminium alloy hereinafter referred to as liquid aluminium.

This aluminium alloy can contain magnesium at a non-zero and even very low content Y, of the order of 20 ppm. According to a further embodiment, the content Y is greater than or equal to 0.05%, preferably greater than 0.5%, and more preferably greater than or equal to 0.7% by weight.

However, the liquid metal can also be sodium, zinc, or another metal, and the sonotrode made of steel or titanium or any other substantially inert metal, i.e. not dissolving significantly in the liquid metal, or of ceramic and in particular a silicon nitride or a silicon oxynitride, such as SIALON.

Advantageously, the method comprises before step d), a step comprising the arrangement, in the liquid metal, of a calibration reflector, preferably inert with respect to said metal, and step d) comprises a reflection step by the reflector of the measurement ultrasounds transmitted by the sonotrode, so as to generate an ultrasonic signal, the method comprising a step for triggering the application of the power ultrasounds according to step d) when the ultrasonic signal generated has an intensity less than or equal to a predetermined threshold intensity.

According to a preferential embodiment, the liquid metal is liquid aluminium.

According to a further embodiment, the liquid metal is sodium, zinc, or another metal, and the sonotrode made of steel or titanium or any other substantially inert metal, i.e. not dissolving significantly in the liquid metal, or of ceramic and in particular a silicon nitride or a silicon oxynitride, such as SIALON.

As such, when, over time, the wetting of the sonotrode decreases and the ultrasounds are carried into the bath with a reduced intensity, the intensity of the ultrasonic signal reflected by the reflector decreases, automatically the application of power ultrasounds is triggered so as to regenerate the wetting of the sonotrode by the liquid metal over a long period and thereby stabilise the transmission of the ultrasounds over time.

According to one option, the application of the power ultrasounds in step e) is activated periodically, particularly with a frequency between a few seconds and a few hours, typically between 30 minutes and 6 hours. Indeed, this design makes it possible to regenerate the wetting of the sonotrode for use over a long period with a stable signal over time.

Preferably, the application of power ultrasounds according to step e) is carried out over a period of a few seconds to a few minutes, typically around one minute. Indeed, this period is sufficient to maintain wetting under excellent conditions.

The method comprises, before step e), a step for attaching a measurement ultrasound emission transducer to the sonotrode according to an axial assembly. This type of assembly advantageously makes it possible to obtain directional acoustic wave emission or reception.

Similarly, advantageously, the method comprises, before steps c) and e), a step for axial assembly of a power ultrasound emission transducer on said sonotrode in addition to the measurement or testing ultrasound emission transducer. As such, the measurement and power transducers are attached to the same sonotrode according to an axial assembly.

According to one option, the attachment is obtained by bonding the measurement transducer to the sonotrode optionally via a flange. According to a further option, the attachment is obtained by screwing the transducer onto the cylindrical flange intimately bonded to the sonotrode. This design makes it possible to ensure durable mechanical coupling between the transducers and sonotrode for liquid aluminium quality measurements, such as the detection of inclusions, Doppler sonic velocimetry, hydrophony in the liquid metal.

According to a further option, the flange is assembled with the sonotrode by "brazing" and in the latter case, the sonotrode is previously partially immersed in a liquid aluminium bath comprising at least 0.05% by weight of magnesium, is subjected to power ultrasounds until the wetting of the sonotrode by liquid aluminium is obtained, and the liquid aluminium is cooled and solidified with the formation of an intimate bond between the sonotrode and the aluminium which is then machined in the form of a flange.

The flange formed in this way has a bonding energy with the sonotrode having similar properties to those obtained upon brazing between two metals. A polished section of the interface obtained using this method between the sonotrode bonded to the metal, observed by scanning electron microscopy (SEM) indeed shows sealing with a perfect bond, without any decohesion and a continuity between the two materials so as to enable optimal mechanical coupling between the metal and the sonotrode. As such, the intimate bond between the sonotrode and the flange has a bonding strength at least substantially equal to that of brazing between the two materials, i.e. it is impossible to detach the flange from the sonotrode without stripping of material.

According to one embodiment option, the liquid metal is in motion.

Advantageously, step d) comprises the Doppler ultrasound velocimetry measurement of the liquid metal.

According to a further option, step d) comprises the detection and measurement of inclusions in the liquid metal. This detection can take place in-line or at a fixed station.

According to one embodiment, the liquid metal is liquid aluminium.

According to a further embodiment, said liquid metal is sodium or zinc, and the sonotrode made of steel or another metal not wetted by sodium or zinc respectively, or of Sialon.

Further aspects, aims and advantages of the present invention will emerge more clearly on reading the following description of three embodiments thereof, given by way of non-limiting example and with reference to the appended figures. The figures do not necessarily observe the scale of the elements represented so as to improve the legibility thereof. Hereinafter in the description, for the purposes of simplification, identical, similar or equivalent elements of the various embodiments bear the same reference numbers.

FIGS. 1 to 3 illustrate schematically the manufacture of an item of equipment comprising a sonotrode for producing an embodiment of the method according to the invention.

FIG. 4 illustrates a first embodiment of the invention.

Figure 5:
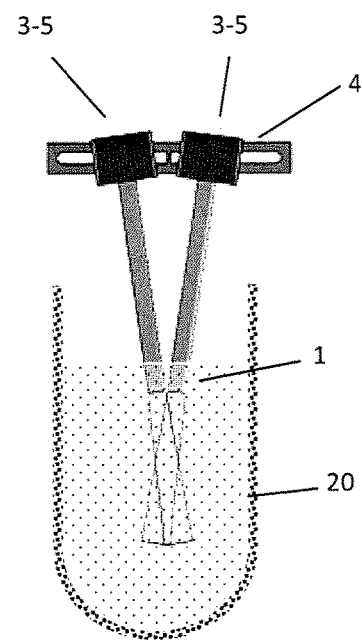
Figure 6:
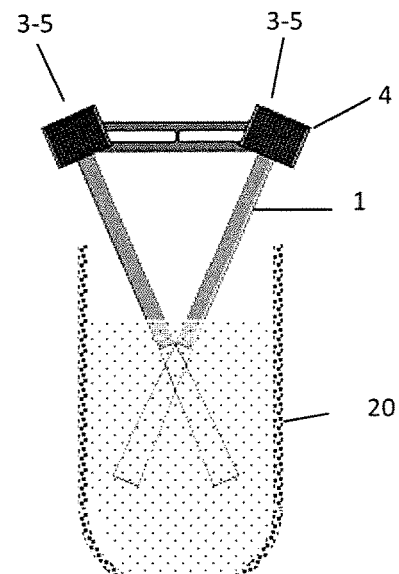

FIGS. 5 and 6 illustrate a second embodiment of the invention.

Figure 7:
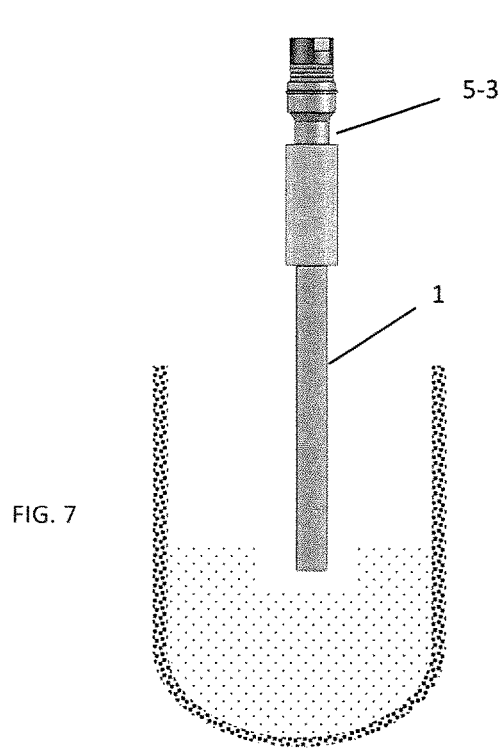

FIG. 7 illustrates a third embodiment of the invention.

As illustrated in FIGS. 1 to 3, a sonotrode 1 of $Si_3N_4$ is wetted in a liquid aluminium alloy bath with a view to use with maintained wetting.

FIG. 1 represents the insertion of a first end region 1a of the cylindrical sonotrode 1, the latter having a length of 400 mm and a diameter of 30 mm, in a crucible 2 containing 3 kg of liquid aluminium, in this instance of the Al5% Mg type including approximately 5% magnesium by weight.

A power ultrasound emission transducer 3 assembled with the sonotrode 1 according to a lateral mode transmits power ultrasounds of a frequency of 19.8 kHz and a power of approximately 150 W to the sonotrode 1 for 5 minutes.

When the sonotrode 1 is removed from the bath in this step of the method, the sonotrode exhibits perfect wetting by the liquid aluminium, identifiable to the naked eye by the shiny light grey colour thereof, characteristic of aluminium, and above all not separable from the ceramic surface using a tool without material stripping.

Obviously, further wetting conditions can be used, with a more or less significant content particularly of magnesium, and preferably a minimum content of 0.05% by weight.

The power ultrasounds are adapted accordingly to the magnesium content used. They are particularly applied for a more or less long time so as to obtain cavitation in the liquid aluminium generating wetting of the sonotrode 1.

According to one option not illustrated, the application of ultrasounds is performed using a power ultrasound transducer 3 attached to the sonotrode 1 according to an axial mode, by fastening or by bonding or by screwing or any other option insofar as the attachment withstands the duration of the operation, typically less than 15 min.

In the next step, the liquid aluminium is cooled around the wetted sonotrode 1 (the sonotrode 1 has not been removed from the bath to check the wetting in this case). The aluminium solidifies and leads to the formation of an intimate bond around the sonotrode 1. The solidified aluminium is then machined in the form of a cylindrical flange 4 around the sonotrode 1.

As represented in FIG. 3, a power ultrasound emission transducer 3 and a measurement ultrasound emission transducer 5 are screwed onto the aluminium flange 4 according to an axial assembly.

The second end region 1b of the sonotrode 1, opposite the first end region 1a attached to the flange 4 is then immersed in an aluminium alloy, and power ultrasounds are applied in order to obtain the wetting of this second end region 1b (step c).

Once the sonotrode has been wetted by the liquid aluminium, measurement ultrasounds are applied by means of the measurement ultrasound emission transducer 5. These ultrasounds applied with a frequency of 5 MHz particularly make it possible to analyse the inclusion quality (quantification and size of inclusions) in the liquid aluminium alloy continuously, particularly over several hours (step d).

Ultrasounds are applied with a power greater than 10 W, by means of the aluminium flange 4 (step e). This ensures the regeneration of the wetting in the liquid aluminium alloy. A hypothesis that can be formulated lies in that, during the use of sonotrode in testing or measurement mode, an oxide film is formed on the surface and alters the wetting. It is assumed that the new application of ultrasounds makes it possible to fragment this oxide film and regenerate the liquid aluminium/wetting aluminium contact of the sonotrode once the sonotrode 1 has been immersed in the alloy. The hypothesis of the accumulation of gas in the vicinity of the sonotrode is likewise not to be ruled out.

Power ultrasounds are thus emitted with a frequency of approximately 20 kHz periodically, particularly every 3 hours for a period of approximately one 1 minute so as to maintain the wetting of the sonotrode 1.

Indeed, it would appear that the periodical application of power ultrasounds makes it possible to "clean" the sonotrode 1—liquid aluminium interface of any inclusion or bubble of gas deposited therein during the use of the sonotrode in the liquid aluminium.

The process is similar in the case where the liquid metal is sodium or zinc, and the sonotrode made of steel or another metal not wetted by Zn or Na respectively, or of ceramic, particularly Sialon.

According to a further option not illustrated, the ultrasounds are emitted intermittently, according to the intensity of the signal received in return when a measurement ultrasound calibration reflector is used in the bath containing the alloy.

It is as such possible to use the sonotrode 1 for different applications.

Measurements of the inclusion quality can particularly be carried out continuously, for the duration of at least one casting, and over a large volume fraction, due, in particular, to the excellent ultrasound transmission in the liquid metal.

FIGS. 5 and 6 illustrate an embodiment applied in particular to the measurement of the inclusion quality of a liquid aluminium alloy, but applicable to any liquid metal or sonotrode inert with respect to the latter. Two sonotrodes 1 made of Si3N4 (length 400 mm diameter 30 mm), wetted by prior application of power ultrasounds, are herein partially immersed in a crucible 20 comprising 25 kg of liquid aluminium alloy. The power ultrasound transducer 3 is attached according to an axial assembly to the cylindrical flange 4 on each thereof. A measurement ultrasound emission transducer 5 is arranged in the flange 4 in contact with the bar of a sonotrode 1 of Si3N4.

The sonotrode 1, whereon the measurement ultrasound emission transducer 5 is attached, is used for the emission of the measurement ultrasounds whereas the other sonotrode 1 is used in reception mode. The tandem assembly of the two sonotrodes 1 makes it possible, by modifying the angle and the gap between the sonotrodes 1, to obtain geometric focussing of the ultrasound beam. A small gap between the sonotrodes 1 and a small angle α make it possible to increase the volume of aluminium alloy tested but the limit of detection is increased in terms of inclusion size such that the detection actually has a lower sensitivity (FIG. 5). Conversely, a large gap between the sonotrodes 1 and a significant angle α make it possible to reduce the tested volume and the limit of detection is lowered (FIG. 6). In the latter case, the detection sensitivity is greater.

After introducing the sonotrodes 1 into the liquid aluminium alloy, with a gap of 300 mm and an angle α of 28°, the sonic measurement signal is not significantly present. The liquid aluminium alloy A does not wet the sonotrodes 1. The application of power ultrasounds (19.8 kHz, 150 W, 5 seconds) to the sonotrode 1 operating in emission mode followed by the application of power ultrasounds to the sonotrode 1 operating in reception mode makes it possible to establish wetting: as such, there is subsequently transmission of the ultrasonic measurement signal (5 MHz). In this case, the noise level detected increases and peaks corresponding to unitary particles (inclusions) appear. The regular application of power ultrasounds makes it possible to maintain wetting and a continuity in the detection and quantification of inclusions, also known as inclusion cleanliness measurement, in an in-line or fixed liquid aluminium alloy bath.

According to a further embodiment of the method illustrated in FIG. 7, the sonotrode 1 is used for the purposes of Doppler effect ultrasound velocimetry of a bath of liquid aluminium alloy in motion, which was hitherto reliably restricted to metals with a low melting point.

In this embodiment, a power ultrasound transducer 3 and a measurement ultrasound emission transducer 5 are attached according to an axial assembly to a sonotrode 1 made of SIALON and power ultrasounds (20 kHz, 120 W, 8 s) are applied to establish wetting.

Measurement ultrasounds, having the same characteristics as above, are applied continuously and the variation of the frequency of the ultrasonic signal is measurement by means of the transducer 3 which also operates in reception mode. In parallel, the power ultrasounds are applied every five hours to maintain the wetting of the sonotrode 1 (step e). The progression of the frequency reflected by the suspended particles, with respect to the emitted frequency, is modelled on the displacement of the particles induced by the fluid.

As such, the present invention relates to the use of a method for using a sonotrode 1 wetted by liquid aluminium, applicable to a measurement method comprising the continuous use of an apparatus for measuring inclusions in a liquid aluminium alloy, which offers the option of switching from a measurement mode (measurement ultrasounds) to a wetting regeneration mode (power ultrasounds) without having to intervene on the apparatus, which remains immersed and is autonomous.

Furthermore, the sonotrodes 1 do not require any surface treatment to chemically modify the surface of the refractory material forming the sonotrode 1.

It is then possible to use this method for continuous non-destructive testing of the liquid aluminium alloy and for analysis, particularly of the inclusion quality of the aluminium by means of wetting regeneration.

Advantageously, the measurement equipment used for the method comprises in a preferred embodiment an assembly wherein the sonotrode 1 and the ultrasound transducers 3, 5 (measurement and power) form a single entity.

Similarly, the method can be used in the case wherein said liquid metal is sodium or zinc, and the sonotrode made of steel or another metal not wetted by sodium or zinc respectively, or of Sialon.

It is obvious that the invention is not limited to the embodiment described above by way of example but that it includes any technical equivalents and the alternative embodiments of the means described as well as the combinations thereof.

The invention claimed is:

1. A method for sonic testing of a liquid metal comprising:
   a) providing a sonotrode formed from a substantially inert material with respect to the liquid metal, wherein the sonotrode is selected from the group consisting of a ceramic and a metal substantially inert to said liquid metal,
   b) immersing at least partially the sonotrode in a bath of said metal,
   c) applying to the sonotrode power ultrasounds to obtain wetting of said sonotrode by said metal,
   d) applying continuously to the sonotrode measurement ultrasounds and/or testing ultrasounds,
   e) applying intermittently to the sonotrode power ultrasounds to maintain said wetting.

2. The method according to claim 1, wherein the liquid metal is a liquid aluminium alloy.

3. The method according to claim 2, wherein the liquid metal, at least in c), is a liquid aluminium alloy containing magnesium at a content Y, the magnesium content Y being different than zero.

4. The method according to claim 3, wherein the content Y is greater than or equal to 0.05%.

5. The method according to claim 1, wherein the liquid metal is sodium or zinc, and the sonotrode is selected from the group consisting of steel, another metal not wetted by sodium or zinc, respectively, and ceramic.

6. The method according to claim 1, comprising, at least from d) the positioning, in said liquid metal, of a calibration reflector for reflecting the measurement ultrasounds transmitted by the sonotrode, so as to generate an ultrasonic signal, and triggering the application of the power ultrasounds according to e) when the ultrasonic signal generated has an intensity less than or equal to a predetermined threshold intensity.

7. The method according to claim 6 wherein said liquid metal is an aluminium alloy.

8. The method according to claim 6, wherein the liquid metal is sodium or zinc, the sonotrode made of steel or another metal not wetted by sodium or zinc respectively, or of SiAlON.

9. The method according to claim 1, wherein the application of the power ultrasounds in e) is activated periodically.

10. The method according to claim 1, wherein the application of power ultrasounds according to e) is carried out over one minute.

11. The method according to claim 1, wherein the method comprises, before c), a step for attaching a power ultrasound emission transducer to the sonotrode according to an axial assembly.

12. The method according to claim 11, wherein the method comprises before d), axial assembly of a measurement ultrasound emission transducer on said sonotrode in addition to the power ultrasound emission transducer.

13. The method according to claim 12, wherein at least one of the two transducers is mounted on a flange, in turn attached to the sonotrode by bonding, banding, screwing or brazing, and in the latter case, the sonotrode is previously partially immersed in a liquid aluminium bath comprising at least 0.05% by weight of magnesium, is subjected to power ultrasounds until the wetting of the sonotrode by liquid aluminium is obtained, and the liquid aluminium is cooled and solidified with the formation of a bond between the sonotrode and the aluminium which is then machined in the form of a flange.

14. The method according to claim 1, wherein said liquid metal is in motion.

15. The method according to claim 14, wherein d) also comprises the Doppler ultrasound velocimetry measurement of said liquid metal in motion.

16. The method according to claim 1, wherein d) also comprises detection and measurement of inclusions in said liquid metal.

17. The method according to claim 9 wherein said liquid metal is an aluminium alloy.

18. The method according to claim 9 wherein said liquid metal is sodium or zinc, and the sonotrode made of steel or another metal not wetted by sodium or zinc respectively, or of SiAlON.

19. The method according to claim 2, wherein in a), the substantially inert material is $Si_3N_4$.

20. The method according to claim 1, wherein the sonotrode is a ceramic selected from the group consisting of silicon nitride and silicon oxynitride.

* * * * *